US008770046B2

United States Patent
Maeda et al.

(10) Patent No.: US 8,770,046 B2
(45) Date of Patent: Jul. 8, 2014

(54) AUTOSAMPLER WITH CONTROL UNIT FOR PERFORMING A CLEANING OPERATION

(75) Inventors: Yoshiaki Maeda, Kyoto (JP); Kenichi Yasunagi, Kyoto (JP); Takafumi Nakamura, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 284 days.

(21) Appl. No.: 13/382,499

(22) PCT Filed: Sep. 1, 2010

(86) PCT No.: PCT/JP2010/064935
§ 371 (c)(1),
(2), (4) Date: Jan. 5, 2012

(87) PCT Pub. No.: WO2011/027784
PCT Pub. Date: Mar. 10, 2011

(65) Prior Publication Data
US 2012/0111127 A1    May 10, 2012

(30) Foreign Application Priority Data
Sep. 7, 2009   (WO) .................. PCT/JP2009/004408

(51) Int. Cl.
*G01N 1/22*    (2006.01)
(52) U.S. Cl.
USPC ...................................................... 73/863.01
(58) Field of Classification Search
CPC .... G01N 30/24; G01N 35/10; G01N 35/1004
USPC .................. 73/863, 863.01, 864.21
See application file for complete search history.

(56) References Cited

U.S. PATENT DOCUMENTS

| 2004/0175833 A1 | 9/2004 | Tatsumi ........................ 436/49 |
| 2008/0134804 A1 | 6/2008 | Maeda et al. ............. 73/863.01 |
| 2010/0098590 A1* | 4/2010 | Inamura et al. ........... 422/82.05 |
| 2010/0326215 A1 | 12/2010 | Maeda et al. ............. 73/864.21 |

FOREIGN PATENT DOCUMENTS

| JP | 55-104761 | 8/1980 |
| JP | 62-203459 | 12/1987 |
| JP | 2004-271241 | 9/2004 |
| JP | 2004-317213 | 11/2004 |

(Continued)

OTHER PUBLICATIONS

Japanese language international preliminary report on patentability dated Apr. 11, 2012 and its English language translation issued in corresponding PCT application PCT/JP2010/064935.

*Primary Examiner* — Hezron E Williams
*Assistant Examiner* — David Z Huang
(74) *Attorney, Agent, or Firm* — Bingham McCutchen LLP

(57) ABSTRACT

An autosampler is provided with a needle, a measuring pump which sucks and discharges liquid through the needle, a movement mechanism for the needle, and an injection port which has a needle sealing surface. A sample liquid is sucked into the needle and then the sample liquid discharged with the tip of the needle pressed to the needle sealing surface. When cleaning the needle sealing surface, a cleaning liquid within the injection port is sucked and then the cleaning liquid is discharged and sucked into the injection port at a position at which the tip of the needle does not make contact with the needle sealing surface. Alternatively, after the cleaning liquid is discharged into the injection port, the needle may be caused to perform an up and down motion such that the tip of the needle contacts the needle sealing surface and then is lifted.

6 Claims, 14 Drawing Sheets

(56) References Cited

FOREIGN PATENT DOCUMENTS

| | | |
|---|---|---|
| JP | 2006-038809 | 2/2006 |
| JP | 3129218 | 1/2007 |
| JP | 2008-145112 | 6/2008 |
| JP | 2008-164498 | 7/2008 |
| JP | 2009-036723 | 2/2009 |
| WO | WO 2009/041441 A1 | 4/2009 |

* cited by examiner

FIG.10

| EQUIPMENT | ITEM | CONDITION |
|---|---|---|
| LIQUID FEED PUMP | MOBILE PHASE | WATER : METHANOL = 8 : 2 |
| | FLOW RATE | 0.3 ml/min. |
| AUTOSAMPLER | LOW-PRESSURE FLOW PATH SOLVENT | CLEANING LIQUID 1: METHANOL |
| | | CLEANING LIQUID 2: WATER : METHANOL = 8 : 2 |
| | | MOBILE PHASE: WATER : METHANOL = 8 : 2 |
| | SAMPLE | 20mg/l AQUEOUS CAFFEINE SOLUTION |
| | | 2000mg/l AQUEOUS CAFFEINE SOLUTION |
| | AMOUNT INJECTED | 5 $\mu$l |
| | SAMPLE SUCTION RATE | 5 $\mu$l/s |
| | NEEDLE CLEANING | NO FLOW PATH CLEANING MECHANISM OF THE PRESENT INVENTION |
| | | NEEDLE AND NEEDLE SEAL CLEANING: NONE |
| | | NO CLEANING INSIDE ANALYSIS FLOW PATH |
| | | HAS FLOW PATH CLEANING MECHANISM OF THE PRESENT INVENTION |
| | | NEEDLE AND NEEDLE SEAL CLEANING: CLEANING USING CLEANING LIQUID 1; CLEANING USING 10 $\mu$l OF DROPLETS |
| | | CLEANING INSIDE ANALYSIS FLOW PATH: CLEANING USING CLEANING LIQUID 1 |
| | REPLACEMENT OF CLEANING LIQUID IN CLEANING PORT | YES |
| | REPLACEMENT OF LIQUID IN SAMPLE MEASURING FLOW PATH | YES |
| | SAMPLE COOLER | OFF |
| | SAMPLE BOTTLE | 1.5mL GLASS SAMPLE BOTTLE (SILICONE SEPTUM) |
| | SAMPLE/BLANK SEALED AMOUNT | 1 mL |
| COLUMN OVEN | SET TEMPERATURE | 40°C |
| | COLUMN | 1.8 $\mu$m ODS; INNER DIAMETER 1.5mm × LENGTH 150mm |
| UV DETECTOR | DETECTED WAVELENGTH | 272 nm |
| | CELL THERMOSTAT TEMPERATURE | 40°C |
| | AUX RANGE | 2 AU/V |
| | RESPONSE | 0.5s |
| DATA PROCESSING | WIDTH | 5 |
| | DRIFT | 0 |
| | T. DBL | 1000 |
| | SLOPE | 200 |
| | MIN. AREA | 10 |
| | STOP TIME | 5 |

FIG.13

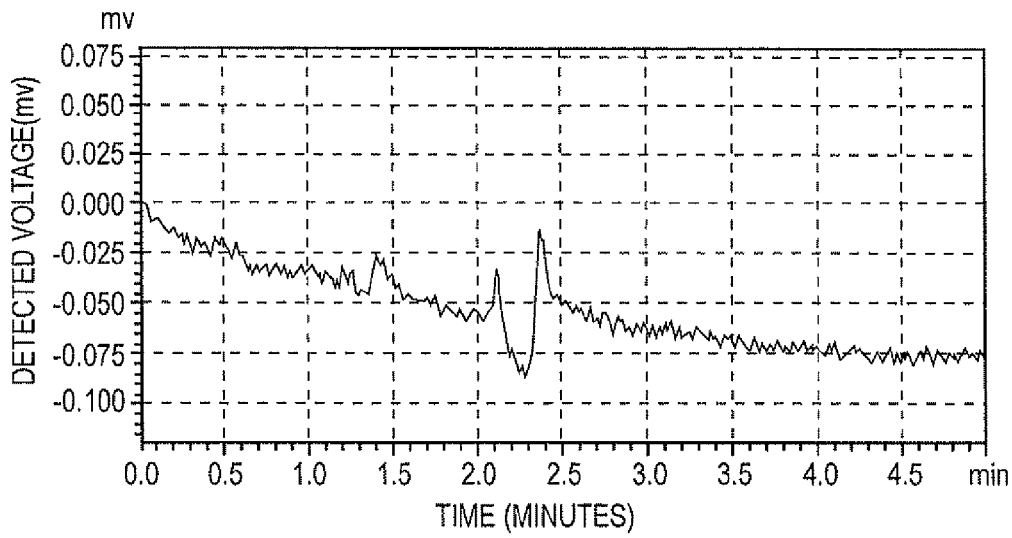

FIG.14

| | ITEM | AREA | RATIO |
|---|---|---|---|
| COMPARISON EXAMPLE | 20 mg/l AQUEOUS CAFFEINE SOLUTION | 269570 | - |
| | 2000 mg/l AQUEOUS CAFFEINE SOLUTION | NOT MEASURABLE | - |
| | BLANK SOLUTION: 1st PASS | 383 | 0.0014% |
| | BLANK SOLUTION: 2nd PASS | 396 | 0.0015% |
| | BLANK SOLUTION: 3rd PASS | 268 | 0.0010% |
| | BLANK SOLUTION: 4th PASS | 253 | 0.0009% |
| | BLANK SOLUTION: 5th PASS | 149 | 0.0006% |
| EMBODIMENTS | 20 mg/l AQUEOUS CAFFEINE SOLUTION | 274784 | - |
| | 2000 mg/l AQUEOUS CAFFEINE SOLUTION | NOT MEASURABLE | - |
| | BLANK SOLUTION: 1st PASS | 214 | 0.0008% |
| | BLANK SOLUTION: 2nd PASS | 92 | 0.0003% |
| | BLANK SOLUTION: 3rd PASS | 96 | 0.0003% |
| | BLANK SOLUTION: 4th PASS | 0 | UNDETECTED |
| | BLANK SOLUTION: 5th PASS | 0 | UNDETECTED |

AUTOSAMPLER WITH CONTROL UNIT FOR PERFORMING A CLEANING OPERATION

CROSS-REFERENCE TO THE RELATED APPLICATIONS

This application is a national stage of international application No. PCT/JP2010/064935, filed on Sep. 1, 2010, and claims the benefit of priority under 35 USC 119 to international application No. PCT/JP20091004408, filed on Sep. 7, 2009, the entire contents of which are incorporated herein by reference.

FIELD OF THE TECHNOLOGY

The present invention relates to an autosampler that is used to automatically collect and introduce sample solutions to analytic instruments used for the analysis of liquids such as a liquid chromatograph.

BACKGROUND ART

With a liquid chromatograph, an autosampler is used so that one liquid sample among a plurality of liquid samples is automatically selected and introduced into a column. FIGS. 1A and 1B show a schematic views of the flow path of an autosampler in a previous liquid chromatograph.

In FIGS. 1A and 1B, high-pressure valve 1 is a flow path switching valve having 6 ports, a through f, and low-pressure valve 2 is a flow path switching valve having 7 ports, g through m. In high-pressure valve 1, port a is connected to a mobile phase flow path to which a mobile phase is supplied; port b is connected to needle 11; port c is connected to port k of low-pressure valve 2; port d is connected to a drain via a solenoid valve 12; port e is connected to an injection port 13; and port f is connected to a flow path that leads to a column. At low-pressure valve 2, port g is connected to a mobile phase; ports h and i are connected to cleaning liquids R1 and R2, respectively; port j is connected to a measuring-pump 14; port k is connected to port c of high-pressure valve 1; port l is connected to a cleaning port 15; and port m is constructed to be connectable to any one of ports g through l while connecting adjacent ports g through l to each other.

FIG. 2 is a block diagram schematically showing a control system for the autosampler. High-pressure valve 1, low-pressure valve 2, measuring-pump 14 and a movement mechanism 6 of needle 11 are connected to a control unit 7. Control unit 7 selects and switches the ports of high-pressure valve 1 and low-pressure valve 2, drives a plunger of measuring-pump 14 and controls the movement of needle 11.

The basic operation of the afore-described autosampler involved in the introduction of samples is described next. To collect a sample, the respective ports of high-pressure valve 1 and low-pressure valve 2 are connected as shown in FIG. 1A to establish a load mode. Needle 11 is then moved to a position above a sample vial, and the tip of needle 11 is inserted into a sample solution. (This is the state shown by the dotted lines in FIG. 1A.) When the plunger of measuring-pump 14 is withdrawn in this state, a predetermined amount of sample solution is drawn in by suction from the vial via a mobile phase (or a cleaning liquid having the same components) that fills the flow path leading from measuring-pump 14 to needle 11 and fills sample loop 16.

After the sample is collected, needle 11 returns to injection port 13 and is connected to injection port 13, switching the connection state of the respective ports of high-pressure valve 1 to that shown in FIG. 1B (injection mode). When this happens, the mobile phase that is supplied from a liquid feeding pump 3 is sent to column 4 via sample loop 16, needle 11 and injection port 13. The sample solution that fills sample loop 16 is supplied to column 4 together with the mobile phase and is separated into components as the sample solution passes through column 4. The components are then sequentially detected by detectors that are not illustrated.

Needle 11 to which a sample solution is adhered due to the afore-described sample collection operation is cleaned in the following way. First, port m and port h of low-pressure valve 2 are connected. The plunger of measuring-pump 14 is withdrawn in this state to draw in cleaning liquid R1 by suction (FIG. 3A). Next, after port m and port l of low-pressure valve 2 are connected, the plunger of measuring-pump 14 is pushed down (FIG. 3B). This causes cleaning liquid R1 to be drawn into and to be held inside cleaning port 15. Next, needle 11 is moved to a position above cleaning port 15 and is immersed into and is cleaned by the cleaning liquid that is present in cleaning port 15. While needle ills so immersed, the cleaning liquid is made to flow into cleaning port 15 from the bottom of cleaning port 15 and to flow out from the top of cleaning port 15 so that the cleaning liquid in cleaning port 15 is kept always clean, thus increasing the cleaning effect on the tip of needle 11. Methods for cleaning the needle proposed in the past include those where a plurality of cleaning methods is used for the cleaning (e.g., Patent Literature 1) and a method where the needle is cleaned by using a high flow rate for the cleaning liquid (e.g., Patent Literature 2).

After needle 11 has been cleaned for a predetermined amount of time by the cleaning liquid, needle 11 is moved to injection port 13. The waste cleaning liquid is discharged to a drain from cleaning port 15.

With the afore-described autosampler, the afore-described cleaning operation of needle 11 is performed every time after the completion of the introduction of a sample. This significantly reduces the cross-contamination of the next sample solution by the previous sample solution but does not completely eliminate the cross-contamination because of the following reasons.

FIG. 4 shows an enlarged view of the connection area between injection port 13 and needle 11. A through-hole 17 is formed through the center of injection port 13. A funnel-shaped sealing-surface 18 is formed at the upper end of through-hole 17. Because the tip of needle 11 is tapered, as needle 11 is lowered and inserted into through-hole 17 of injection port 13, there comes a point where needle 11 has been lowered enough to form a liquid-tight contact and seal between the outer peripheral surface of the tip of needle 11 and sealing-surface 18.

When a sample solution is drawn in by suction from a vial, some of the sample solution adheres to the outer peripheral surface of the tip of needle 11. Because needle 11 is inserted in this condition into injection port 13, some of the sample solution adheres to a part ("contact point 19") of sealing-surface 18 that comes into contact with needle 11. Even when a mobile phase flows from needle 11 to through-hole 17 of injection port 13, the sample solution that was present at contact point 19 is not washed away by the mobile phase and remains there. This means that when the next sample solution is introduced into injection port 13 by needle 11, it becomes possible for the sample solution that remained on contact point 19 of sealing-surface 18 to be pushed by needle 11 into and mixed with the flow path.

One solution that has been proposed to solve problems such as this is to clean sealing-surface 18 by introducing a cleaning liquid into injection port 13 from needle 11 while keeping the tip of needle 11 slightly elevated above sealing-surface 18 (see Patent Literature 3). When doing this, any cleaning liquid that is introduced into injection port 13 that overflows from injection port 13 contaminates the surrounding areas. To address this problem, with the autosampler according to Patent Literature 3, injection port 13 is surrounded by a partition and the cleaning liquid that overflows into the partitioned area is forcibly expelled by an air pump to prevent contamination by the cleaning liquid (waste cleaning liquid).

PRIOR ART LITERATURE

Patent Literature

Patent Literature 1: Unexamined Patent Application Publication No. 2004-271241
Patent Literature 2: Unexamined Patent Application Publication No. 2008-145112
Patent Literature 3: Utility Model Registration Publication No. 3129218

SUMMARY OF THE INVENTION

Problems to Be Solved by the Invention

However, the area around injection port 13 has a complicated structure to begin with, and the addition of a partition and structures required for expelling the cleaning liquid from the partitioned area would make the structure even more complicated. Another problem of providing additional structures is the resulting increased size of injection port 13.

The present invention was made in light of the afore-described problems, and it is the object of the present invention to provide an autosampler wherein the needle-sealing surface of an injection port can be cleaned in an injection port having a simple construction.

Means for Solving the Problems

An autosampler according to a first mode of the present invention includes:
a needle whose tip is formed to be tapered;
a measuring-pump for discharging and drawing in by suction a liquid through the needle;
a movement mechanism for moving the needle in a horizontal direction and a vertical direction;
an injection port having a needle-sealing surface and connected to an analysis flow path via a valve; and
a control unit for controlling the measuring-pump and the movement mechanism;
wherein,
after a sample solution that is held in a sample vessel is drawn in by suction through the needle, the tip of the needle is pressed against the needle-sealing surface and the sample solution is discharged so that the sample solution is introduced into the analysis flow path through the injection port; and
the control unit performs a cleaning operation for cleaning the needle-sealing surface by causing the measuring-pump to draw in by suction an amount of the cleaning liquid that can be held within the injection port, then causing the needle to be moved to a position where the tip of the needle does not contact the needle-sealing surface and then causing the measuring-pump to cause a discharge and suction of the cleaning liquid into and from the injection port through the needle.

A second mode of an autosampler according to the present invention is the autosampler according to the first mode wherein the control unit causes the cleaning operation to be performed a plurality of times.

A third mode of an autosampler according to the present invention is the autosampler according to the first or the second mode wherein the needle is gradually lowered when a cleaning operation is performed by the control unit.

An autosampler according to a fourth mode of the present invention is the autosampler according to the first through the third modes wherein, when the control unit performs a cleaning operation, an up-and-down motion of the needle involving lowering the needle to a position where the tip of the needle comes into contact with the needle-sealing surface and then raising the needle to a position where the tip of the needle is not in contact with the needle-sealing surface is performed once or a plurality of times during the time from the discharge of the cleaning liquid to the suction of the cleaning liquid by the measuring pump.

An autosampler according to a fifth mode of the present invention includes:
a needle whose tip is formed to be tapered;
a measuring-pump for discharging and drawing in by suction a liquid through the needle;
a movement mechanism for moving the needle in a horizontal direction and a vertical direction;
an injection port having a needle-sealing surface and connected to an analysis flow path via a valve; and
a control unit for controlling the measuring-pump and the movement mechanism;
wherein, after a sample solution that is held in a sample vessel is drawn in by suction through the needle, the tip of the needle is pressed against the needle-sealing surface and the sample solution is discharged so that the sample solution is introduced into the analysis flow path through the injection port; and
the control unit performs a cleaning operation for cleaning the needle-sealing surface by causing the measuring-pump to draw in by suction an amount of the cleaning liquid that can be held within the injection port, then causing the needle to be moved to a position where the tip of the needle does not contact the needle-sealing surface, then causing the measuring-pump to discharge the cleaning liquid, then raising the needle to a position where the tip of the needle is not in contact with the surface of the cleaning liquid that is held within the injection port, and then causing the measuring-pump to draw air in by suction and then discharge the air.

An autosampler according to a sixth mode of the present invention is the autosampler according to the first through the fifth modes wherein the control unit cleans the interior of an analysis flow path by causing the tip of the needle to be pressed against the needle-sealing surface and causing the measuring-pump to discharge and draw in by suction the cleaning liquid into and from the injection port through the needle.

Effects of the Invention

With the present invention, an autosampler uses a measuring-pump, which is provided in advance to draw a sample into a needle by suction, to draw in a precise amount of a cleaning liquid by suction so that when the cleaning liquid is discharged into the injection port from the needle, the cleaning liquid does not overflow from the injection port. Because of this, no additional structure is required for preventing the cleaning liquid from overflowing from the injection port during the cleaning operation of the sealing-surface of the needle. Furthermore, because cleaning is performed using suction and discharge over a limited range and without using a separate pump for the cleaning operation, the amount of cleaning liquid that is used for cleaning the sealing-surface of the needle is reduced.

Furthermore, since, with the autosampler according to the present invention, a measuring-pump is used to clean the interior of the analysis flow path, the amount of cleaning liquid that is required for cleaning the analysis flow path can be precisely measured and introduced into the analysis flow path, thus reducing the amount of cleaning liquid that is used for cleaning the analysis flow path. When doing this, since the measuring-pump draws in and discharges the cleaning liquid from the needle and the cleaning liquid is made to move within the analysis flow path in both directions, the analysis flow path can be efficiently cleaned even when using a small amount of the cleaning liquid.

BRIEF DESCRIPTION OF THE FIGURES

FIG. 1 shows a schematic view of one example of a flow path in an autosampler used with previous liquid chromatographs.

FIG. 10 shows a table summarizing the cleaning conditions and the analysis conditions for a liquid chromatograph that uses an autosampler according to embodiment 1.

FIG. 13 shows one example of a chromatogram of a mobile phase that was obtained when the mobile phase was introduced into a liquid chromatograph after a sample had been introduced into the liquid chromatograph using an embodiment of an autosampler according to the present invention.

FIG. 14 shows the results of the analysis obtained with the comparison example and with embodiment 1.

DETAILED DESCRIPTION OF THE INVENTION

Figure 1A:
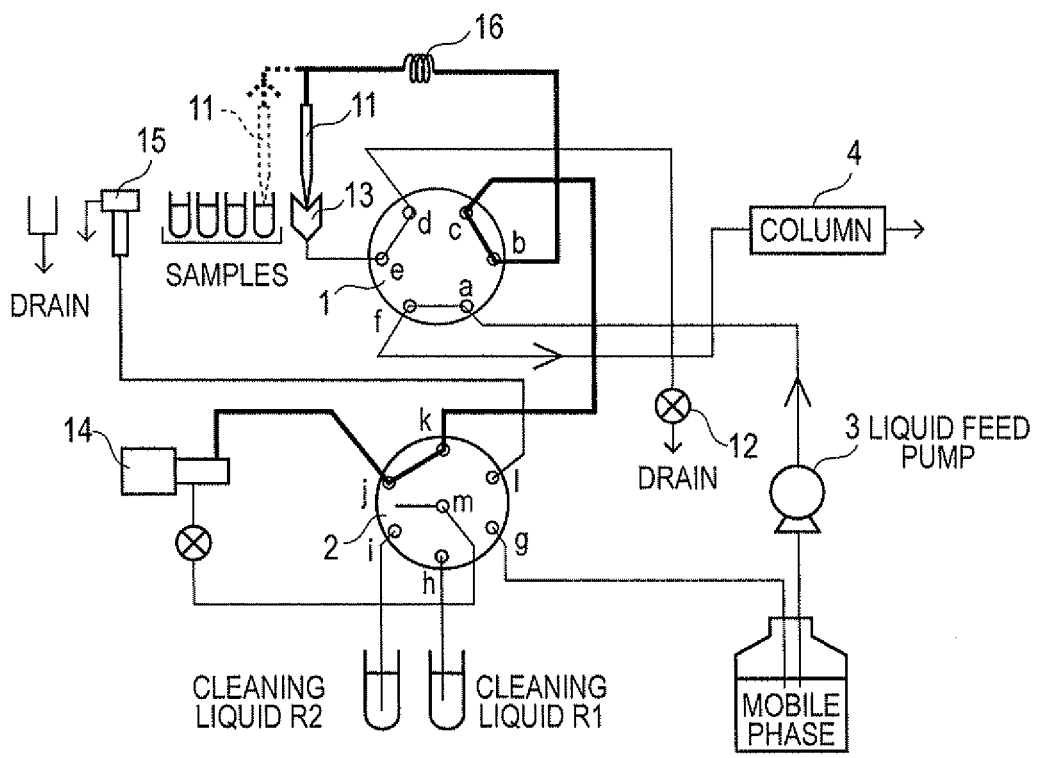
FIG. 1A shows the load mode.
Figure 1B:
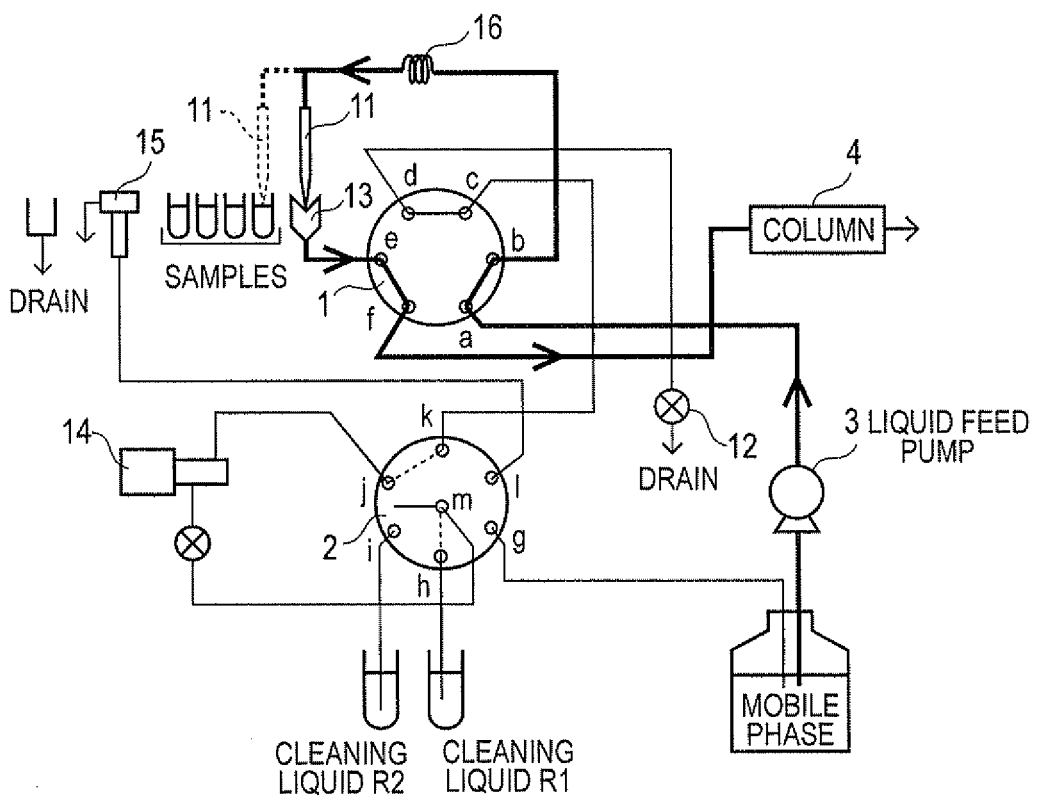
FIG. 1B shows the injection mode.
Figure 2:
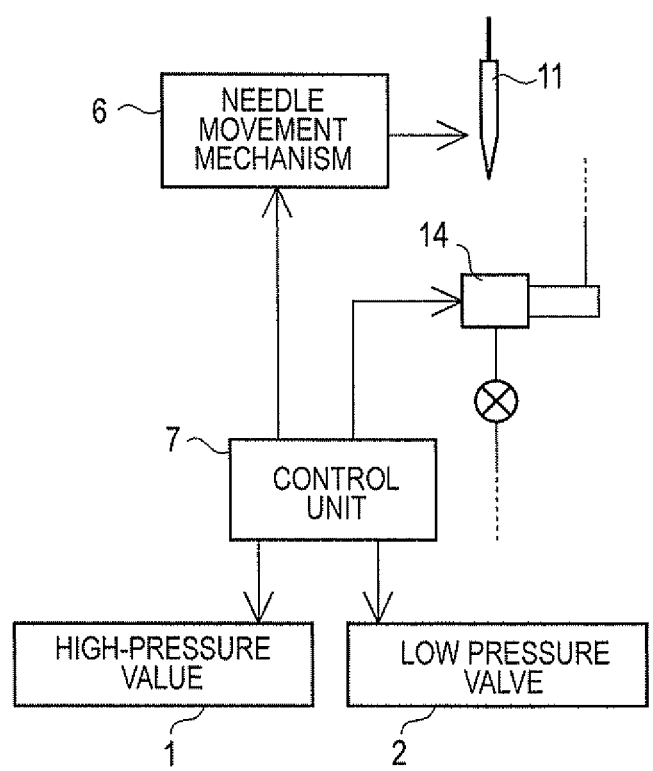
FIG. 2 shows a schematic view of the control mechanism used for the autosampler.
Figure 3A:
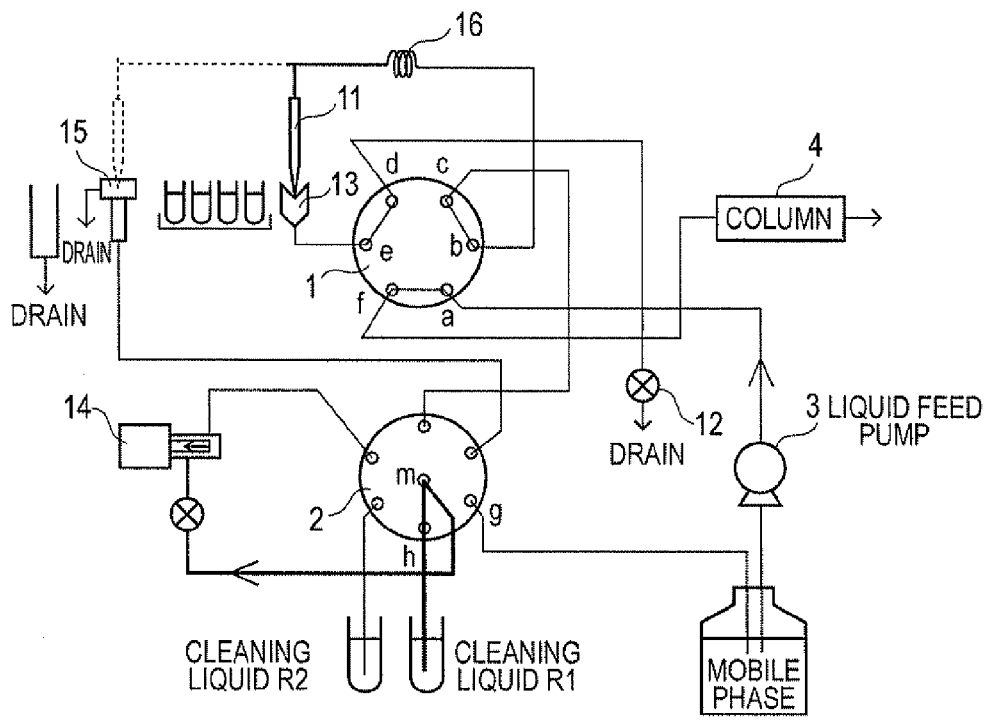
FIG. 3A shows a flow path depicting the operation performed by the measuring-pump of an autosampler used in previous liquid chromatographs for the suction and holding of a cleaning liquid.
Figure 3B:
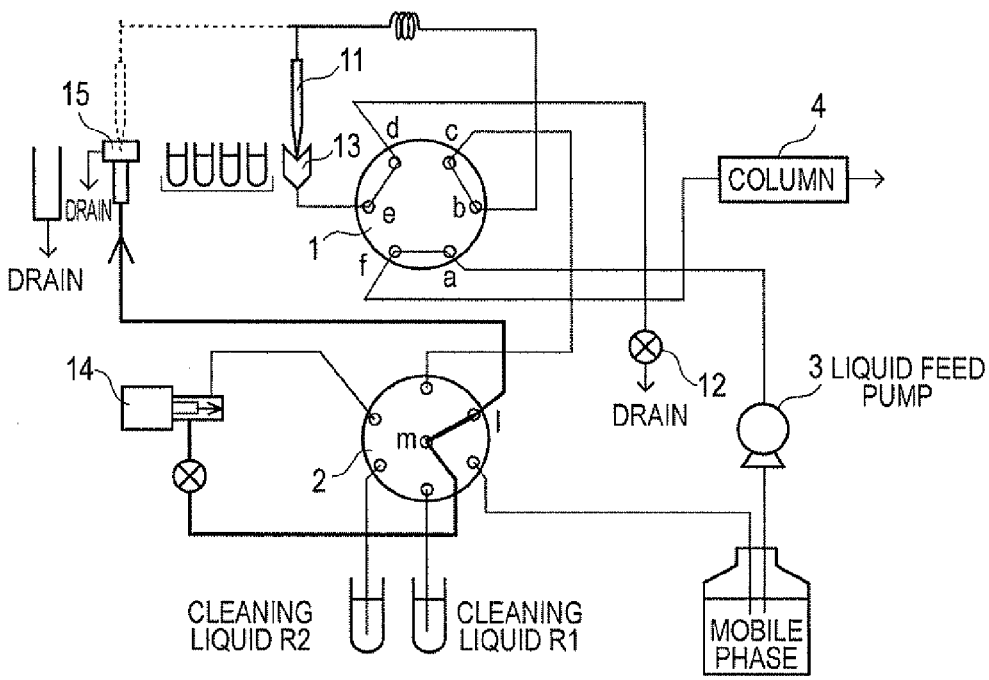
FIG. 3B shows a flow path depicting the operation performed by the measuring-pump to discharge a cleaning liquid from the needle to the cleaning port.
Figure 4:
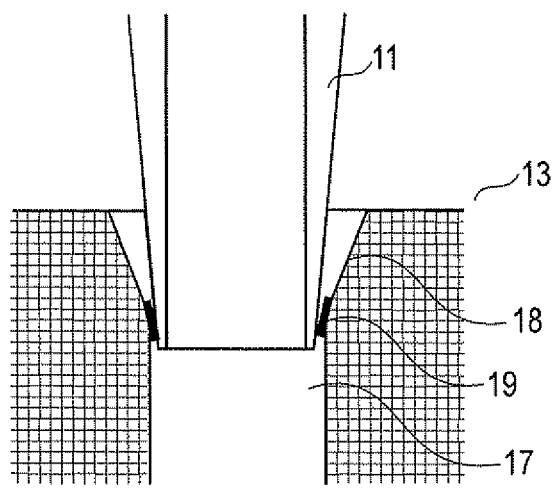
FIG. 4 shows an enlarged sectional view of the connection area between the needle and the injection port.

Embodiments 1 through 3 of an autosampler according to the present invention are described next with reference to FIG. 5A, FIG. 5B and FIG. 6 through FIG. 16D.

Embodiments 1 through 3 of the autosampler are characterized by the cleaning operation that is performed after the collection of a sample. The structure of the flow path is substantially identical to that of a previous autosampler shown in FIG. 1A through FIG. 4. Furthermore, the construction of the high-pressure valves, low-pressure valves, needles and the like that make up the autosampler is substantially identical to that of previous autosamplers. Hence, the description below of the respective embodiments of the autosampler centers primarily on the cleaning operation. In the description below, the same numerical references are used for the same parts shown in FIG. 1A through FIG. 4 of a previous autosampler.

With embodiments 1 through 3 of the autosampler, after the sample is collected, the control unit 7 controls the movement of needle 11, the switching of the ports for high-pressure valve 1 and low-pressure valve 2, and the driving of measuring-pump 14 and performs a cleaning operation on needle 11 and needle-sealing surface 18 and a cleaning operation on the analysis flow path. In the description below, the cleaning operation performed on needle 11 and needle-sealing surface 18 is referred to as the "needle cleaning operation," and the cleaning operation performed on the analysis flow path is referred to as the "flow path cleaning operation."

Embodiment 1

The needle cleaning operation is described next with reference to FIG. 5A, FIG. 5B, FIG. 6 and FIG. 7. With the needle cleaning operation, needle-sealing surface 18 is cleaned after cleaning the outer peripheral surface of the tip of needle 11.

Figure 5A:
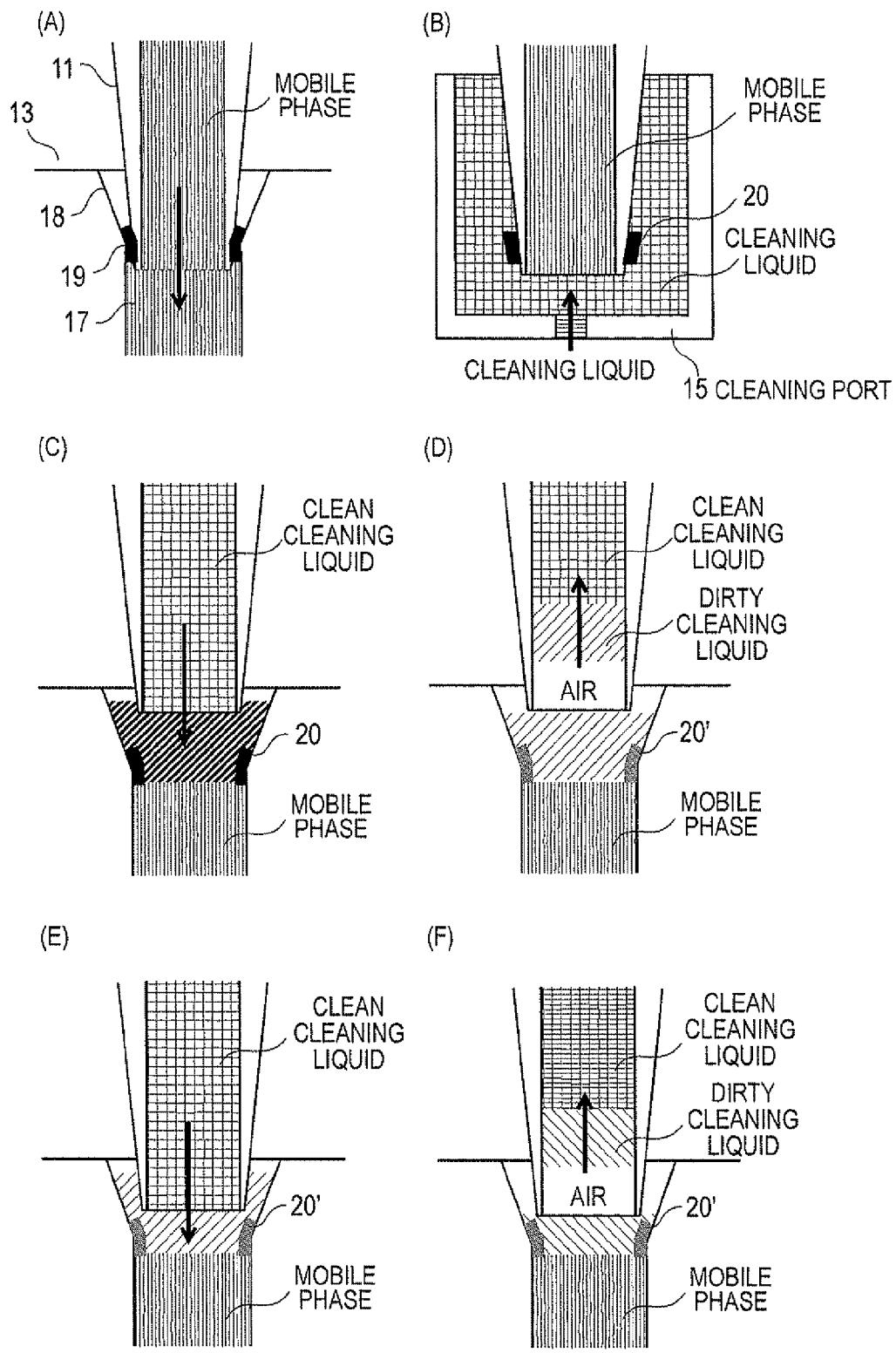
FIG. 5A depicts the cleaning operation of the needle and the needle-sealing surface according to embodiment 1 of the present invention (No. 1).

As afore-described, after the sample is collected, the respective ports of high-pressure valve 1 are switched to the injection mode (see FIGS. 1A and B), and needle 11 is connected to injection port 13 (FIG. 5A (a)). When this happens, the sample solution that is present in sample loop 16 is introduced into column 4 together with the mobile phase. This is followed by switching high-pressure valve 1 to the load mode and sequentially switching the connection state of the ports of low-pressure valve 2 from the state shown in FIG. 3A to the state shown in FIG. 3B. Needle 11 is then moved to cleaning port 15 and is immersed into the cleaning liquid that is in cleaning port 15 to clean contamination 20 that is adhered to the outer peripheral surface of the tip of needle 11 (FIG. 5A (b)).

After the outer peripheral surface of the tip of needle 11 is cleaned, a cleaning operation is performed to clean contamination 20 that is adhered to needle-sealing surface 18. With the cleaning operation of needle-sealing surface 18, needle 11 is first lowered to a position such that the tip of the needle does not contact needle-sealing surface 18, for example, to a position where needle 11 is located 1 mm above contact point 19. The plunger of measuring-pump 14 is then pushed out to discharge a cleaning liquid from the tip of needle 11 towards injection port 13. Because the mobile phase has been introduced into through-hole 17 of injection port 13 to a position close to contact point 19, the cleaning liquid that is discharged into injection port 13 is held in a portion of injection port 13 that is located above contact point 19 (FIG. 5A(c)). The amount by which the plunger of measuring-pump 14 is pushed out (i.e., the quantity discharged from needle 11) is set so that the cleaning liquid that is discharged from needle 11 does not overflow from injection port 13 while at the same time the tip of needle 11 is immersed in the cleaning liquid. Holding the cleaning liquid cleans needle-sealing surface 18 and removes contamination 20 that is adhered to contact point 19.

The plunger of measuring-pump 14 is then withdrawn so as to draw by suction into needle 11 the cleaning liquid and air that are present in injection port 13 (FIG. 5A(d)). At this time, because needle 11 is held at the same vertical position as when discharging the cleaning liquid, some of the cleaning liquid in injection port 13 are not drawn in by suction and remains within injection port 13. When the afore-described cleaning operation of needle-sealing surface 18 is completed, needle 11 is lowered slightly, and the cleaning operation of needle-sealing surface 18 is repeated.

With embodiment 1, the cleaning operation of needle-sealing surface 18 is performed three times. The needle 11 is lowered slightly after the completion of the first and the second cleaning operations. For example, if the tip of needle 11 is located at a position 1 mm above contact point 19 for the first cleaning operation, needle 11 is lowered so that the tip of needle 11 is located 0.6 mm above contact point 19 for the second cleaning operation and is located 0.3 mm above for the third cleaning operation (FIGS. 5A(e) and (f), and FIGS. 5B(g) and (h)). At any of the positions, the tip of needle 11 is located above and is not in contact with needle-sealing surface 18. The operations for the discharge and suction of the cleaning liquid through needle 11 are the same as the first cleaning operation. Any contamination 20' that remains at contact point 19 after the first cleaning operation is removed nearly completely by the second and third cleaning operations.

Figure 5B:
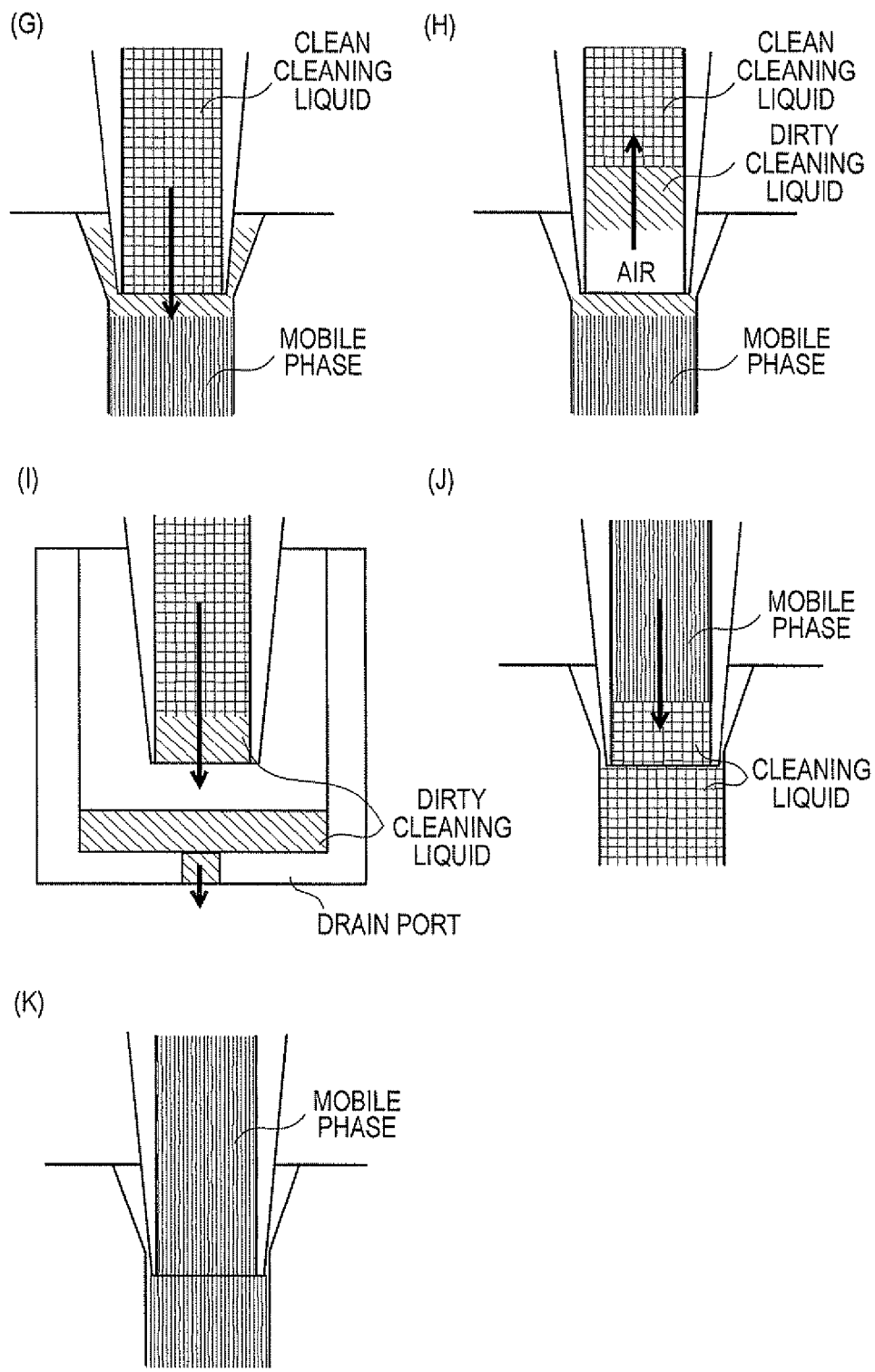
FIG. 5B depicts the cleaning operation of the needle and the needle-sealing surface according to embodiment 1 of the present invention (No. 2).

After the cleaning operation is completed, needle 11 is moved to drain port 5 (see FIG. 6) where the cleaning liquid (waste cleaning liquid) present within needle 11 is discharged into drain port 5 by measuring-pump 14 (FIG. 5B(i)).

By repeating the operation of discharging from and drawing in by suction of the cleaning liquid into injection port 13 while keeping needle 11 at a vertical position not to contact needle-sealing surface 18, needle-sealing surface 18 that previously would not have come into contact with the cleaning liquid is cleaned, and contamination 20 that is adhered to contact point 19 of needle-sealing surface 18 is nearly completely removed. Because the drawing in by suction and discharging of the cleaning liquid are performed over only a limited range of needle-sealing surface 18, the amount of cleaning liquid that is consumed is reduced. Furthermore, by lowering the position of needle 11 by a slight amount after each cleaning operation, the waste cleaning liquid is drawn in by suction with greater certainty.

Figure 6:
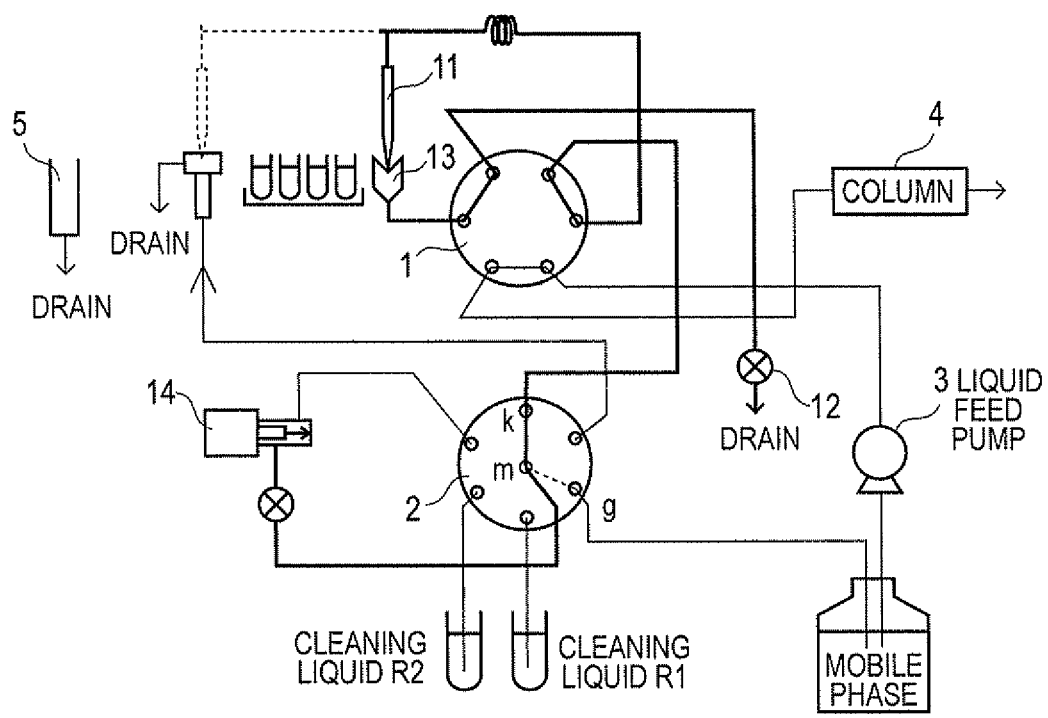
FIG. 6 shows the flow path when in state (j) depicted in FIG. 5B.

After the cleaning liquid in needle 11 is discharged into drain port 5, needle 11 is returned from drain port 5 to injection port 13 and is lowered until a tight contact is formed with needle-sealing surface 18 (FIG. 5B (j)). While maintaining this state, port m and port g of low-pressure valve 2 are connected, and the plunger of measuring-pump 14 is withdrawn so as to draw the mobile phase into measuring-pump 14 by suction where the mobile phase is held. Then, as shown in FIG. 6, port m and port k of low-pressure valve 2 are connected, and high-pressure valve 1 is switched to the load mode to discharge the mobile phase in measuring-pump 14. This causes the cleaning liquid present within needle 11, injection port 13 and the respective flow paths to be replaced by the mobile phase (FIG. 5B (k)).

Thereafter, high-pressure valve 1 is switched to the injection mode (see FIG. 1B), and needle 11 is connected to liquid feeding pump 3 in preparation for the next sample injection operation.

The flow path cleaning operation is described next with reference to FIG. 7 through FIG. 9.

Figure 7:
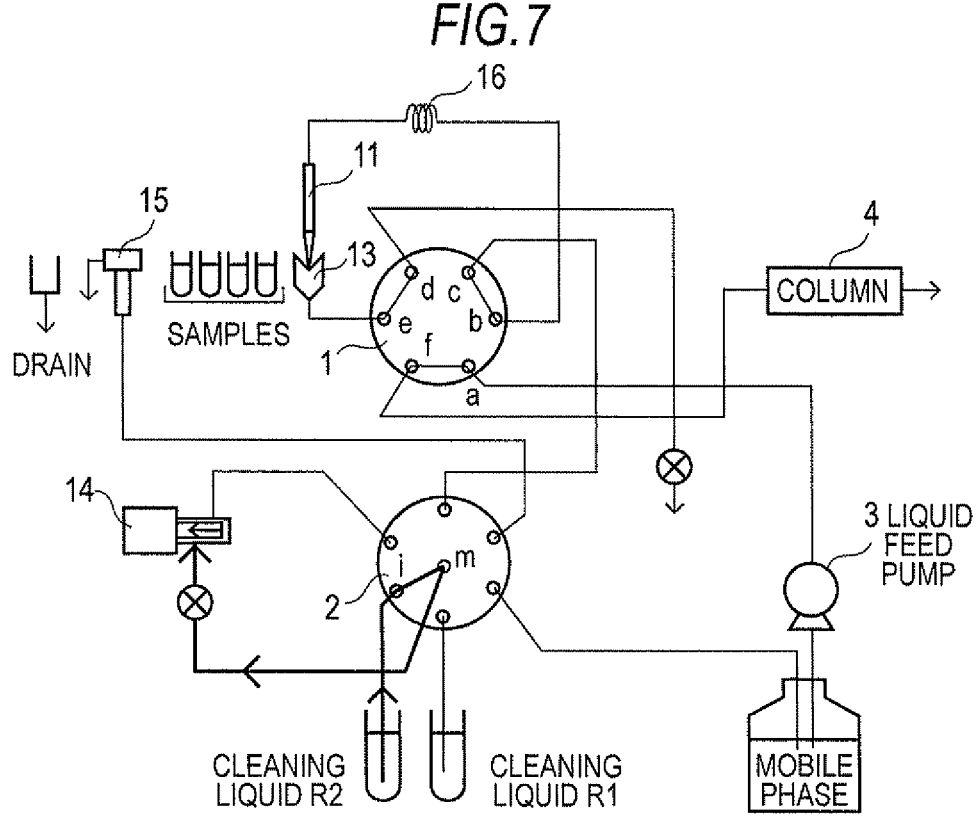
FIG. 7 shows the flow path used during a flow path cleaning operation for the measuring-pump to draw in a cleaning liquid by suction and to hold the cleaning liquid.
Figure 8:
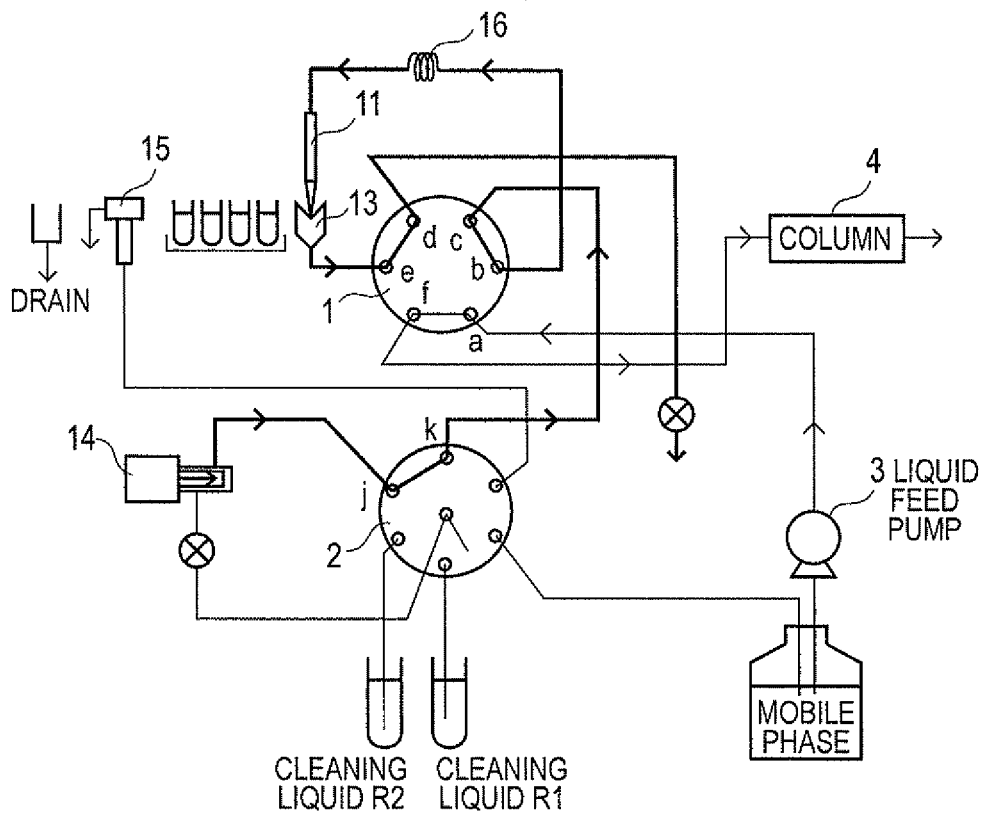
FIG. 8 shows the flow path used during a flow path cleaning operation for replacing the mobile phase present in the analysis flow path with a cleaning liquid.

First, the plunger of measuring-pump 14 is withdrawn while port m and port i of low-pressure valve 2 are connected so as to draw cleaning liquid R2 by suction into measuring-pump 14 where the cleaning liquid is held (FIG. 7).

Figure 9:
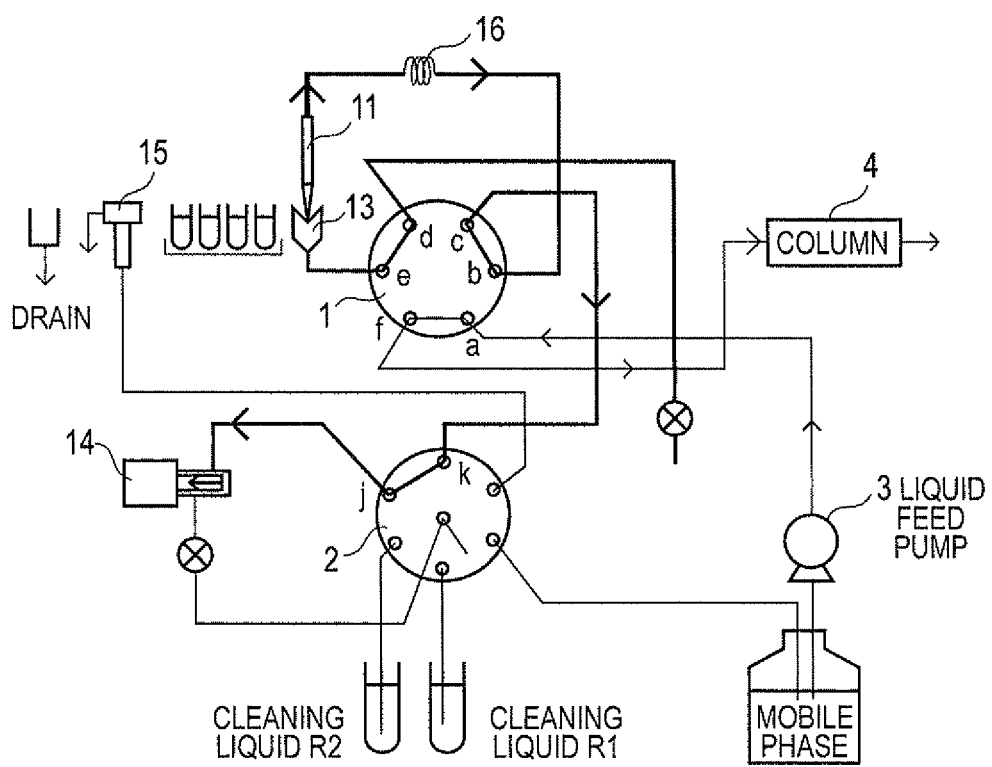
FIG. 9 shows the flow path during a flow path cleaning operation for the measuring-pump to draw in by suction the cleaning liquid that is present in the analysis flow path.

Then, the connection between port m and port i of low-pressure valve 2 is released, port j and port k are connected, and high-pressure valve 1 is set to the load mode (FIG. 9). The plunger of measuring-pump 14 is pushed out in this state to discharge cleaning liquid R2 that is held within measuring-pump 14 into sample loop 16, needle 11 and the flow path that passes through injection port 13 so as to replace the sample that is present within the flow path with cleaning liquid R2 (discharge operation). The amount of cleaning liquid that is expelled from measuring-pump 14 is set to be enough (e.g., 200 µl) for the replacement of the sample that is present within the flow path.

Next, while holding high-pressure valve 1 and low-pressure valve 2 in the same state, the plunger of measuring-pump 14 is withdrawn so as to draw in the cleaning liquid present in the flow path by suction (suction operation (reverse cleaning operation), FIG. 9). This causes the cleaning liquid in the flow path to move in a direction opposite to its movement direction during the discharge operation where the plunger is pushed out. The amount of cleaning liquid that is drawn in by suction by measuring-pump 14 during this operation is set to be much less (e.g., several dozen µl) than the amount of cleaning liquid that was discharged during the discharge operation.

Subsequently, the plunger of measuring-pump 14 is pushed out so as to discharge the cleaning liquid again into the flow path in an amount that exceeds the amount that was drawn in by suction (FIG. 9).

The afore-described suction operation and discharge operation of the cleaning liquid by measuring-pump 14 are repeated multiple times. This causes the cleaning liquid to flow within the flow path in a forward direction and an opposite backward direction, thus cleaning the flow path.

Specifically, by moving the cleaning liquid in the forward and backward directions in the flow path, residual liquids that tend to stagnate at the joints between different components that make up the flow path are efficiently washed away.

Furthermore, since the cleaning liquid is repeatedly made to flow in the flow path in the forward and backward directions, the interior of the flow path can be cleaned while using only a small amount of the cleaning liquid.

Furthermore, since the interior of the flow path is cleaned using only a small amount of the cleaning liquid, a measuring-pump 14 which is used for introducing the sample and which is suited for flowing relatively small amounts of liquids can be used for the cleaning operation, thus obviating the need for providing a separate liquid feeding pump specifically for cleaning the interior of the flow path.

Furthermore, since the amount of the cleaning liquid that is discharged by the measuring-pump is greater than the amount of the cleaning liquid that is drawn in by suction, the repetition of the discharge operation and the suction operation causes the residual liquid that is stagnating in the flow path to be gradually moved and efficiently washed away from the flow path.

When the flow path cleaning operation is completed, measuring-pump 14 discharges the mobile phase to replace the cleaning liquid in the flow path with the mobile phase in an operation similar to that performed during the cleaning of needle-sealing surface 18.

Experiments were also performed to investigate the effect of the autosampler according to the present embodiment in reducing cross-contamination. In this experiment, samples featuring an aqueous caffeine solution with a concentration of 20 mg/l and an aqueous caffeine solution with a concentration of 2000 mg/l and a blank sample (mobile phase only) were sequentially introduced into a liquid chromatograph and analyzed. The analysis of the blank sample was repeated 5 times. Every time that the analysis of the respective samples and the blank sample was completed, the afore-described cleaning operation (needle cleaning operation and flow path cleaning operation) was performed. As a comparison example, analyses were also performed without implementing a cleaning operation. The analysis conditions are shown in FIG. 10.

With these experiments, using the 2000 mg/l aqueous caffeine solution sample, the cross-contamination reduction effect was evaluated using the ratio of peak area α of the aqueous caffeine solution sample to peak area β of the blank sample (i.e., β/α). However, since the peak voltage value of the 2000 mg/l aqueous caffeine solution exceeded the upper limit value, peak area α of the 2000 mg/l aqueous caffeine solution was determined by increasing the peak area of the 20 mg/l aqueous caffeine solution by 100-fold.

Figure 11:
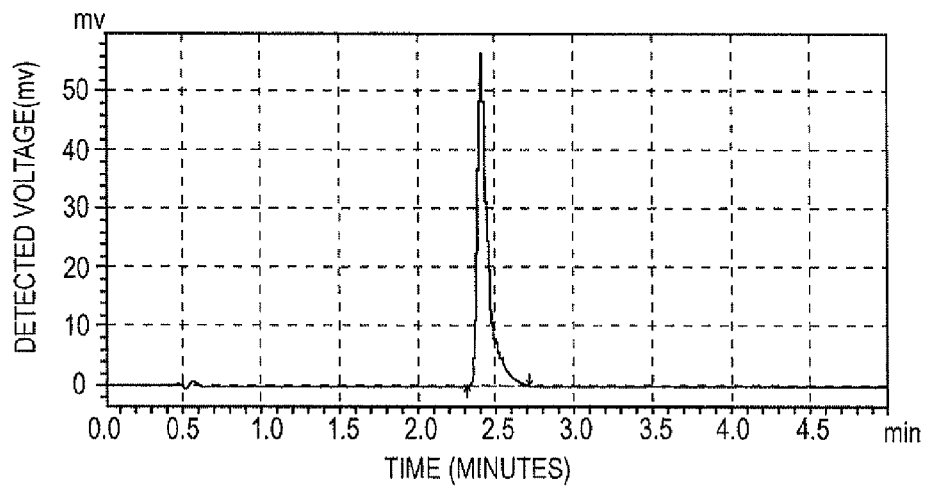
FIG. 11 shows one example of a chromatogram that was obtained when a sample (20 mg/l aqueous caffeine solution) was introduced to a liquid chromatograph using an autosampler according to embodiment 1.
Figure 12:
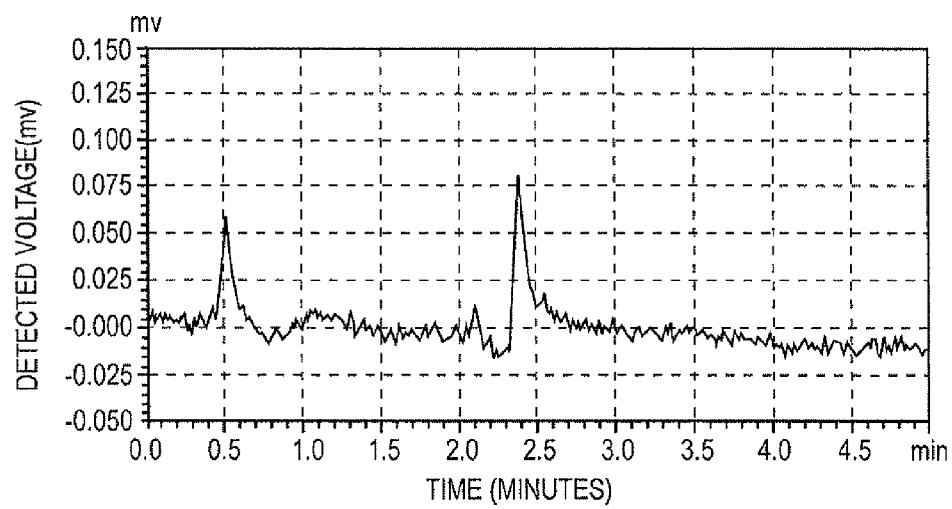
FIG. 12 shows one example of a chromatogram of a mobile phase that was obtained when the mobile phase was introduced into a liquid chromatograph after a sample had been introduced to the liquid chromatograph using an autosampler serving as a comparison example.

FIG. 11 shows one example of a chromatogram representing the result of the analysis of the 20 mg/l aqueous caffeine solution. FIG. 11 shows that the peak for the caffeine occurs about 2.3 to 2.7 minutes after the start of the analysis. FIG. 12 shows a chromatogram representing the result of the first analysis of the blank solution performed using an embodiment of the present invention. FIG. 13 shows a chromatogram representing the result of the first analysis of the blank solution performed using the comparison example. The graduations along the horizontal axis (time axis) of the two chromatograms are identical to those on the horizontal axis of FIG. 11. In each chromatogram of the blank sample, a peak corresponding to caffeine appears about 2.3 minutes to 2.7 minutes after the start of the analysis.

On the other hand, the graduations along the vertical axis serving as the intensity axis of FIG. 12 and FIG. 13 are much smaller in quantity as compared to those of FIG. 11, showing that, for both the comparison example and the embodiments, the peak area of caffeine in the blank sample is greatly reduced as compared to the peak area of the sample (20 mg/l aqueous caffeine solution). Since the quantities represented by the graduations along the vertical axis of FIG. 13 are about one-half of those of FIG. 12, it is evident that the peak area of caffeine in the blank sample is smaller with the embodiments than with the comparison example.

FIG. 14 shows the peak areas for the respective samples for the comparison example and the embodiments, and the values of ratio β/α. FIG. 14 shows that the ratio β/α is much smaller with the embodiments as compared to the comparison example. In particular, with the fourth and fifth analyses of the blank sample using the embodiments, no caffeine was detected, showing that the amount of cross-contamination was greatly reduced with the autosamplers that were the embodiments of the present invention as compared to previous autosamplers.

During the cleaning operation of needle-sealing surface 18 using the afore-described embodiment 1, the position of needle 11 was sequentially lowered while repeating multiple times the discharge and suction of the cleaning liquid. However, it is also acceptable to repeat the discharge and suction operations multiple times while remaining at the same position.

Also, even though the cleaning operation of needle-sealing surface 18 was repeated multiple times with the afore-described embodiment 1, it is also acceptable to perform the cleaning operation only once. In so doing, needle 11 can be positioned at the same place for both the discharge operation and the suction operation of the cleaning liquid, but positioning needle 11 to be lower for the suction operation than for the discharge operation allows the cleaning liquid to be more surely drawn in by suction.

Furthermore, as for the vertical position of needle 11 during a cleaning operation of needle-sealing surface 18, the only requirement is that the position be such that the tip of needle 11 does not contact needle-sealing surface 18. For example, the tip of needle 11 can be positioned above the open end of through-hole 17 of injection port 13. If injection port 13 is completely filled with the cleaning liquid, it is possible for the surface tension of the cleaning liquid to cause the liquid surface to be positioned higher than the open end of through-hole 17. This means that even if the tip of needle 11 is positioned higher than the open end of through-hole 17 of injection port 13, needle 11 is still capable of drawing in the cleaning liquid by suction.

Embodiment 2

The autosampler according to embodiment 2 is the same as that of embodiment 1 except for the difference in the cleaning operation of needle-sealing surface 18. Thus, only the cleaning operation for needle-sealing surface 18 is described here with reference to FIGS. 15A-15E.

Figure 15A:
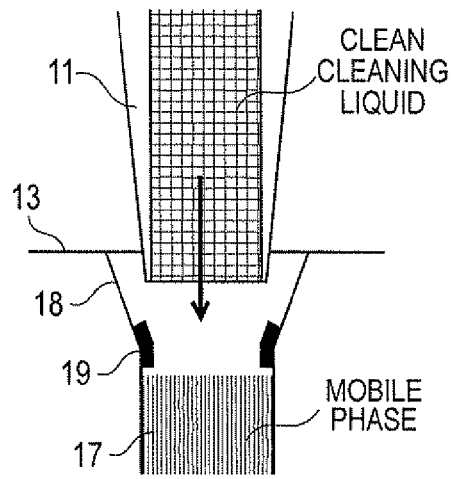
FIG. 15A-15E depicts the cleaning operation for the needle-sealing surface in embodiment 2 of the present invention.
Figure 15B:
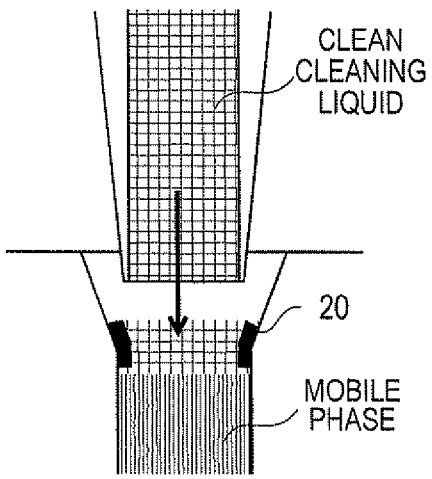

When the cleaning operation of needle 11 is completed, needle 11 is lowered to such a position, just like embodiment 1, that the tip of needle 11 does not contact needle-sealing surface 18 (see FIG. 15A). The plunger of pump 14 is pushed out in this state so that a cleaning liquid is discharged from the tip of needle 11 towards injection port 13 (see FIG. 15B). Because the mobile phase has been introduced into through-hole 17 of injection port 13 to a position close to contact point 19, the cleaning liquid that is discharged into injection port 13 is held in a portion of injection port 13 that is located above contact point 19 (FIG. 5A (c)).

Figure 15C:
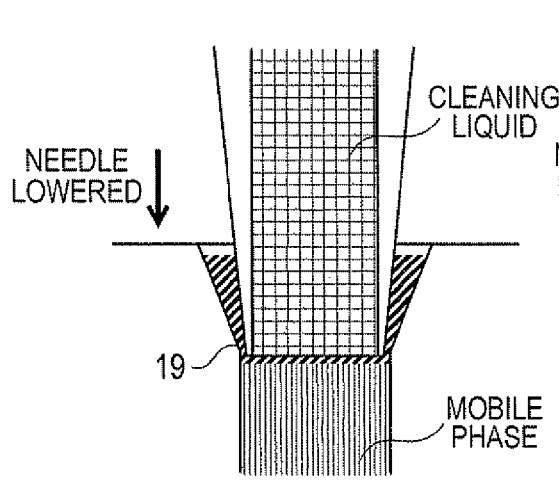

Next, needle 11 is lowered to a position such that the tip of needle 11 contacts needle-sealing surface 18 at contact point 19 (see FIG. 15C). Needle 11 is then raised so that the tip of needle 11 is located above the liquid surface (see FIG. 15D). This is followed by the lowering of needle 11 until its tip again contacts needle-sealing surface 18 (see FIG. 15C). This up-and-down motion of needle 11 is repeated a plurality of times and causes the cleaning liquid that is held within injection port 13 to be agitated. The needle-sealing surface 18 is cleaned and contamination 20 that is adhered to contact point 19 is nearly completely removed by the agitation of the cleaning liquid and the physical contact between the tip of needle 11 and contact point 19.

Figure 15D:
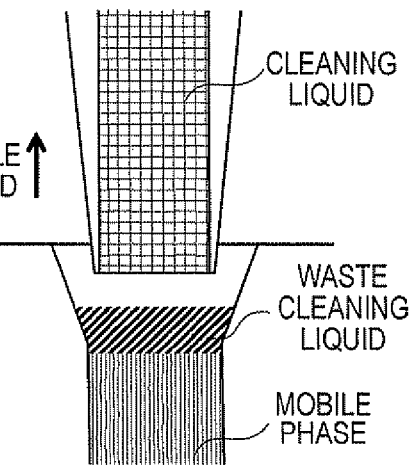
Figure 15E:
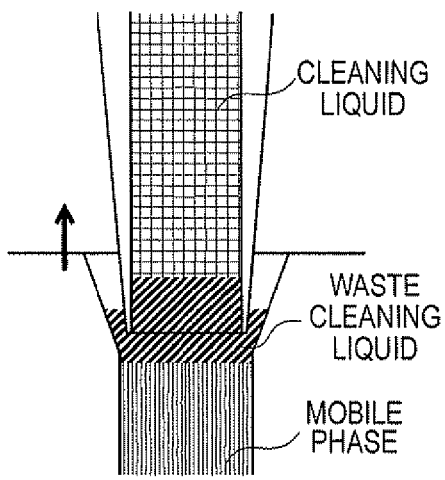

Lastly, with the tip of needle 11 kept at a position slightly away from needle-sealing surface 18, the plunger of measuring-pump 14 is withdrawn so that the cleaning liquid (waste cleaning liquid) that is held in injection port 13 is drawn into needle 11 by suction (see FIG. 15E). This operation causes almost all of the cleaning liquid that is held in injection port 13 to be drawn by suction into needle 11. Subsequently, needle 11 is moved to drain port 5 (see FIG. 6) where measuring-pump 14 causes the cleaning liquid (waste cleaning liquid) in needle 11 to be discharged to drain port 5. After that, using a procedure similar to that of embodiment 1, the cleaning liquid in needle 11, injection port 13 and in the respective flow paths is replaced by the mobile phase.

In the above description of embodiment 2, when needle 11 is raised, needle 11 is raised to a position where the tip of needle 11 is located higher than the surface of the cleaning liquid that is held and discharged (see FIG. 15D). However, it is also acceptable to not raise needle 11 so high that the tip of needle 11 becomes physically separated from the liquid surface but instead to engage in an up-and-down motion with the tip of needle 11 being kept below the surface of the cleaning liquid. Also, the cleaning effect can be further enhanced by repeating the operations from discharging the cleaning liquid into injection port 13 (FIG. 15B) to the drawing in by suction of the waste cleaning liquid (FIG. 15E).

Embodiment 3

The autosampler according to embodiment 3 is the same as that of embodiments 1 and 2 except for the difference in the cleaning operation of needle-sealing surface 18. Thus, only the cleaning operation of needle-sealing surface 18 is described here with reference to FIGS. 16A-16D.

Figure 16A:
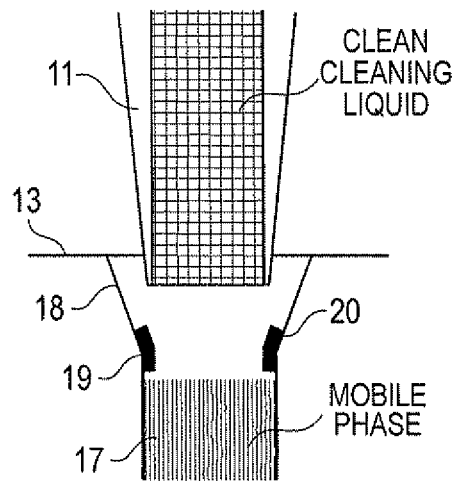
FIG. 16 depicts the cleaning operation for the needle-sealing surface in embodiment 3 of the present invention.

When the cleaning operation of needle 11 is completed, needle 11 is lowered to such a position, just like embodiment 1, that the tip of needle 11 does not contact needle-sealing surface 18 (see FIG. 16A). The plunger of pump 14 is then pushed out so that a cleaning liquid is discharged from the tip of needle 11 towards injection port 13 (see FIG. 16B).

Because the mobile phase has been introduced into through-hole 17 of injection port 13 to a position close to contact point 19, the cleaning liquid that is discharged into injection port 13 is held in a portion of injection port 13 that is located higher than contact point 19. By holding the cleaning liquid, needle-sealing surface 18 is cleaned, and contamination 20 that is adhered to contact point 19 is removed.

Subsequently, needle 11 is raised to a position such that the tip of needle 11 is located above the surface of the cleaning liquid that is held inside injection port 13. The plunger of measuring-pump 14 is then withdrawn so that air is drawn by suction into needle 11 through the tip of needle 11 (see FIG. 16C). The plunger of measuring-pump 14 is then pushed in so that the air that was drawn in by suction is blown towards the surface of the cleaning liquid that is held in injection port 13. This causes the waste cleaning liquid that is held in injection port 13 to be blown away and removed (see FIG. 16D). By adjusting the force with which the air is blown, it is possible to completely blow away and remove the waste cleaning liquid that is held within injection port 13. Because the amount of waste cleaning liquid that is held within injection port 13 is miniscule, it is difficult to contemplate a situation where the waste cleaning liquid that is blown away contaminates the nearby areas to the detriment of the measurement and analysis.

Figure 16B:
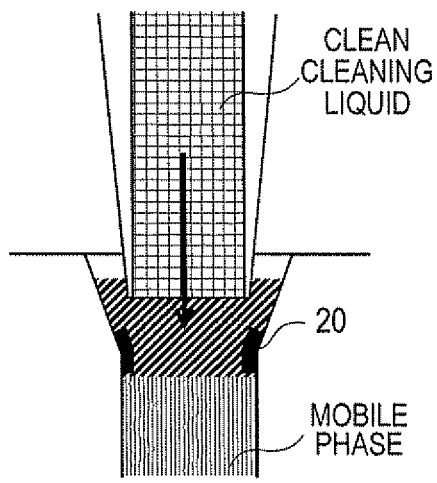
Figure 16C:
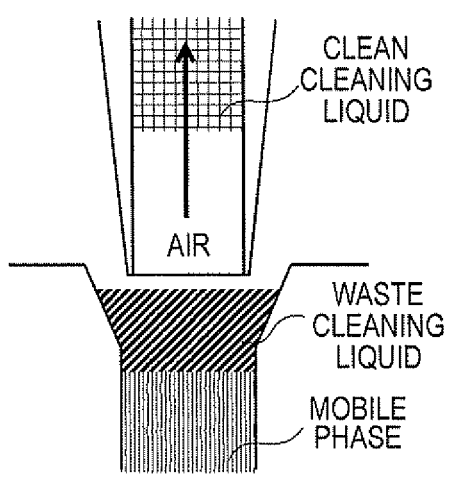
Figure 16D:
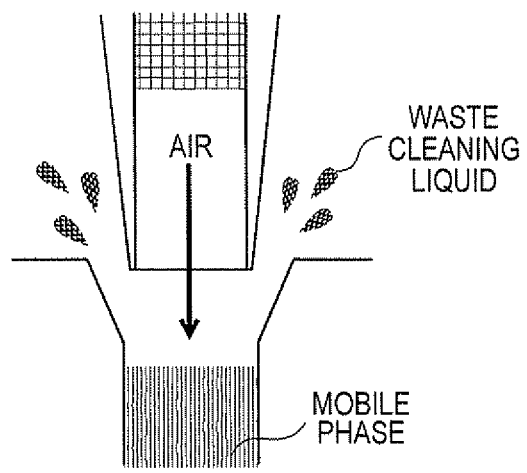

In FIG. 16B, the tip of needle 11 is positioned beneath the surface of the cleaning liquid that is discharged and held within injection port 13. However, it is also acceptable to lower needle 11 such that the tip of needle 11 does not contact the surface of the cleaning liquid that is held within injection port 13. It is also acceptable to repeat multiple times the operations from discharging the cleaning liquid into injection port 13 (FIG. 16B) to the dispersion and removal of the waste cleaning liquid (FIG. 16D) to further enhance the cleaning effect.

The afore-described method used with embodiment 3 for the dispersion and removal of the waste cleaning liquid can also be used in the cleaning operation of the needle-sealing surface in embodiments 1 and 2. To explain, instead of drawing the waste cleaning liquid that is held in the injection port into the needle by suction as is done with embodiments 1 and 2, it is acceptable to disperse and remove the waste cleaning liquid as is done with embodiment 3.

The present invention is not limited to the afore-described embodiments, and the present invention can be suitably modified without deviating from the scope of the present invention.

For example, the description above of the embodiments assumed the use of an autosampler whose flow path construction allowed all of the measured sample to be injected, but as long as the autosampler has a cleaning port, the present invention can be used with an autosampler whose flow path construction involves the injection of only a portion of the measured sample.

DESCRIPTION OF THE NUMERICAL REFERENCES

1. High-pressure valve
2. Low-pressure valve
6. Movement mechanism
7. Control unit
11. Needle
12. Solenoid valve
13. Injection port
14. Measuring pump
15. Cleaning port
16. Sample loop
17. Through-hole
18. Needle sealing surface
19. Contact point
20. Contamination

What is claimed is:
1. An autosampler comprising:
a needle whose tip is formed to be tapered;
a measuring-pump for discharging and drawing in by suction a liquid through said needle;
a movement mechanism for moving said needle in a horizontal direction and a vertical direction;
an injection port having a needle-sealing surface and connected to an analysis flow path via a valve; and
a control unit for controlling said measuring-pump and said movement mechanism,
wherein after a sample solution that is held in a sample vessel is drawn in by suction through said needle, the tip of said needle is pressed against said needle-sealing surface and said sample solution is discharged so that said sample solution is introduced into said analysis flow path through said injection port; and
said control unit performs a cleaning operation for cleaning said needle-sealing surface by causing said measuring-pump to draw in from a cleaning liquid vessel by suction, an amount of a cleaning liquid to be held within said injection port, then causing said needle to be moved to a position where the tip of said needle does not contact said needle-sealing surface and then causing said measuring-pump to cause a discharge and suction of the cleaning liquid into and from said injection port through said needle.

2. The autosampler according to claim 1 wherein said control unit causes said cleaning operation to be performed a plurality of times.

3. The autosampler according to claim 1 or 2 wherein said needle is lowered when a cleaning operation is performed by said control unit.

4. The autosampler according to claim 3 wherein, when said control unit performs a cleaning operation, an up-and-down motion of the needle involving lowering said needle to a position where the tip of said needle comes into contact with said needle-sealing surface and then raising said needle to a position where the tip of the needle is not in contact with said needle-sealing surface is performed once or a plurality of times during the time from the discharge of said cleaning liquid to the suction of said cleaning liquid by said measuring pump.

5. An autosampler comprising:
a needle whose tip is formed to be tapered;
a measuring-pump for discharging and drawing in by suction a liquid through said needle;
a movement mechanism for moving said needle in a horizontal direction and a vertical direction;
an injection port having a needle-sealing surface and connected to an analysis flow path via a valve; and
a control unit for controlling said measuring-pump and said movement mechanism;
wherein after a sample solution that is held in a sample vessel is drawn in by suction through said needle, the tip of said needle is pressed against said needle-sealing surface and said sample solution is discharged so that said sample solution is introduced into said analysis flow path through said injection port; and
said control unit performs a cleaning operation for cleaning said needle-sealing surface by causing said measuring-pump to draw in from a cleaning liquid vessel by suction, an amount of a cleaning liquid to be held within said injection port, then causing said needle to be moved to a position where the tip of said needle does not contact said needle-sealing surface, then causing said measuring-pump to discharge said cleaning liquid, then raising said needle to a position where the tip of said needle is not in contact with the surface of the cleaning liquid that is held within said injection port, and then causing said measuring-pump to draw air in by suction and then discharge the air.

6. The autosampler according to claim 1 wherein said control unit cleans the interior of an analysis flow path by causing the tip of said needle to be pressed against said needle-sealing surface and causing said measuring-pump to discharge into and draw in by suction said cleaning liquid from said injection port through said needle.

* * * * *